US008865722B2

(12) United States Patent
Hrakovsky et al.

(10) Patent No.: US 8,865,722 B2
(45) Date of Patent: Oct. 21, 2014

(54) WET FORMULATIONS OF ARIPIPRAZOLE

(75) Inventors: Julia Hrakovsky, Rosh Ha-Ayin (IL); Ruth Tenengauzer, Raanana (IL)

(73) Assignee: Teva Pharmaceutical Industries Ltd., Petah Tikva (IL)

( * ) Notice: Subject to any disclaimer, the term of this patent is extended or adjusted under 35 U.S.C. 154(b) by 1556 days.

(21) Appl. No.: 11/376,029

(22) Filed: Mar. 14, 2006

(65) Prior Publication Data

US 2007/0154544 A1 Jul. 5, 2007

Related U.S. Application Data

(60) Provisional application No. 60/756,708, filed on Jan. 5, 2006.

(51) Int. Cl.
*A61K 31/497* (2006.01)
*A61K 31/395* (2006.01)
(52) U.S. Cl.
CPC ................................ *A61K 31/395* (2013.01)
USPC ...................................................... 514/252.13
(58) Field of Classification Search
CPC ...................................................... A61K 31/395
USPC ...................................... 424/465; 514/252.13
See application file for complete search history.

(56) References Cited

U.S. PATENT DOCUMENTS

| 6,977,257 | B2 | 12/2005 | Parab et al. | |
|---|---|---|---|---|
| 2002/0076437 | A1* | 6/2002 | Kothari et al. | 424/465 |
| 2004/0058935 | A1* | 3/2004 | Bando et al. | 514/253.07 |
| 2005/0019398 | A1 | 1/2005 | Kotharl et al. | |
| 2005/0089557 | A1 | 4/2005 | Kawasaki | |
| 2005/0148597 | A1 | 7/2005 | Kostanski et al. | |
| 2005/0159429 | A1 | 7/2005 | Parthasaradhi et al. | |
| 2005/0202088 | A1* | 9/2005 | Hanshermann et al. | 424/471 |
| 2005/0203299 | A1* | 9/2005 | Aronhime et al. | 544/262 |
| 2005/0272742 | A1 | 12/2005 | Worthen et al. | |
| 2006/0142299 | A1 | 6/2006 | Ettema et al. | |
| 2006/0142579 | A1 | 6/2006 | Ettema et al. | |
| 2006/0257471 | A1 | 11/2006 | Ettema et al. | |
| 2006/0258673 | A1 | 11/2006 | Ettema et al. | |
| 2006/0270683 | A1 | 11/2006 | Lohray et al. | |
| 2007/0014853 | A1 | 1/2007 | Zalit et al. | |
| 2007/0014854 | A1 | 1/2007 | Zalit et al. | |
| 2007/0014864 | A1 | 1/2007 | Zalit et al. | |
| 2007/0148100 | A1 | 6/2007 | Jenkins | |
| 2007/0148245 | A1 | 6/2007 | Zalit et al. | |
| 2007/0272777 | A1 | 11/2007 | Samburski et al. | |
| 2008/0020038 | A1 | 1/2008 | Stritzke et al. | |
| 2008/0132518 | A1 | 6/2008 | Wieser et al. | |

FOREIGN PATENT DOCUMENTS

| EP | 1145711 | 10/2001 |
|---|---|---|
| EP | 1 475 084 | 11/2004 |
| WO | WO01/08688 | 2/2001 |

(Continued)

OTHER PUBLICATIONS

ABILIFY™ Label (Apr. 8, 2004).*

(Continued)

*Primary Examiner* — Benjamin Packard
(74) *Attorney, Agent, or Firm* — Kenyon & Kenyon LLP

(57) ABSTRACT

The invention encompasses wet granulation pharmaceutical compositions of aripiprazole, methods of making tablets from the compositions, and tablets of the wet granulation pharmaceutical composition.

22 Claims, 1 Drawing Sheet

X-ray Diffractogram of Aripiprazole Type-I.

(56) References Cited

FOREIGN PATENT DOCUMENTS

| WO | WO 03/026659 | 4/2003 |
|---|---|---|
| WO | 2005041937 | 5/2005 |
| WO | WO2005/041935 | 5/2005 |
| WO | WO 2005/058835 | 6/2005 |
| WO | WO 2005/058835 A2 * | 6/2005 |
| WO | WO2005/067976 | 7/2005 |
| WO | 2006097344 | 9/2006 |
| WO | WO 2006/097344 | 9/2006 |
| WO | 2007004061 | 1/2007 |
| WO | 2007011349 | 1/2007 |
| WO | 2007035348 | 3/2007 |
| WO | 2007073389 | 6/2007 |
| WO | 2007092779 | 8/2007 |

OTHER PUBLICATIONS

Crystalline Polymorphism of Organic Compounds, Mino R. Caira, Topics in Current Chemistry, vol. 198, pp. 163-208, Springer Verlag Berlin Heidelberg 1998.

ABILIFY® aripiprazole label, PDR 2004.

Oshiro et al., "Novel Antipsychotic Agents with Dopamine Autoreceptor Agonist Properties: Synthesis and Pharmacology of 7-[4[(4-Phenyl-1piperazinyl)butoxy]-3,4-dihydro-2(1H)-quinolinone Derivatives," J. Med. Chem. 41:658-665 (1998).

Opposition filed against European Patent EP1808164 (06251324.7) by Hexal AG dated Oct. 6, 2009.

Opposition filed against European Patent EP1808164B (06251324.7) by Dr. Markus Breuer dated Oct. 7, 2009.

European Medicines Agency, "Scientific Discussion," pp. 1-29; http://www.emea.europa.eu/htms/human/epar/a.htm (2005).

Pharmazeutische Technologie, Rudolf Voigt, Deutsche Apotheker Verlag, Stuttgart 2000, 9. vollst. uberarb. Aufl., Seite 154.

Arzneiformenlehre, Ein Lehrbuch fur Pharmazeuten, Paul Heinz List, 4. durchges. Auflage, Wissenschaftliche Verlagsgesellschaft, 1985, Stuttgart, Seiten 31-37.

Arzneiforrnenlehre, Ein Lehrbuch fur Pharmazeuten, Paul Heinz List, 4. durchges. Auflage, Wissenschaftliche Verlagsgesellschaft, 1985, Stuttgart, Seite 38.

Aoki et al., Study on Crystal Transformation of Aripiprazol, Proceedings of the Fourth Japan-Korea Symposium on Separation Technology, 937-940 (1996).

Opposition filed by Dr. Markus Breuer, dated Jan. 27, 2010, against related European Patent 1 808 165 (06251325.4).

Copy of U.S. Appl. No. 60/739,640, filed Dec. 3, 2006 (priority to WO 2006/097344).

Register extract of WO 2006/097344 (EP 1 858 514).

Sandell, E., Compendium of Galenical Pharmacy, p. 299, Govi-Velag GMBH, Pharmaceutical Publishing Company (1962).

Hager's Handbook of Pharmaceutical Practice, pp. 708-711 and 827-833, Springer Publishers (1971).

Gstirner, F., Introduction to the Preparation of Drugs, pp. 208-211,Wissenschaftliche Verlagsgesellschaft MBH, Stuttgart (1968).

Ritschel, W.A., The Tablet, vol. 7, pp. 93, 109, 126 with reference to Table 20, and Table 20 according to pp. 126, 152-153, and 192 (1966).

Remington's Pharmaceutical Sciences, 18th Edition, 1990, pp. 1635-1640 and 1644-1645.

Tousey, Michael D., "The Granulation Process 101: Basic Technologies for Tablet Making", Pharmaceutical Technology Tableting & Granulation, 2002, p. 8-13.

Shangraw, R.F. Ch. 4, Compressed Tablets by Direct Compression, in Pharmaceutical Dosage Forms—Tablets, vol. 1, 2E, H.A. Lieberman et al, eds. (1989), pp. 195-246.

Parikh, D. Handbook of Pharmaceutical Granulation Technology, pp. 101-102 (1997).

Wadke et al., "Pharmaceutical Dosage Forms: Tablets, Second Edition vol. 1, Ch. 1, pp. 5-6; 'Preformulation Testing: IV. Particle Size, Shape, and Surface Area,'" Marcel Dekker Inc., New York, 1989.

* cited by examiner

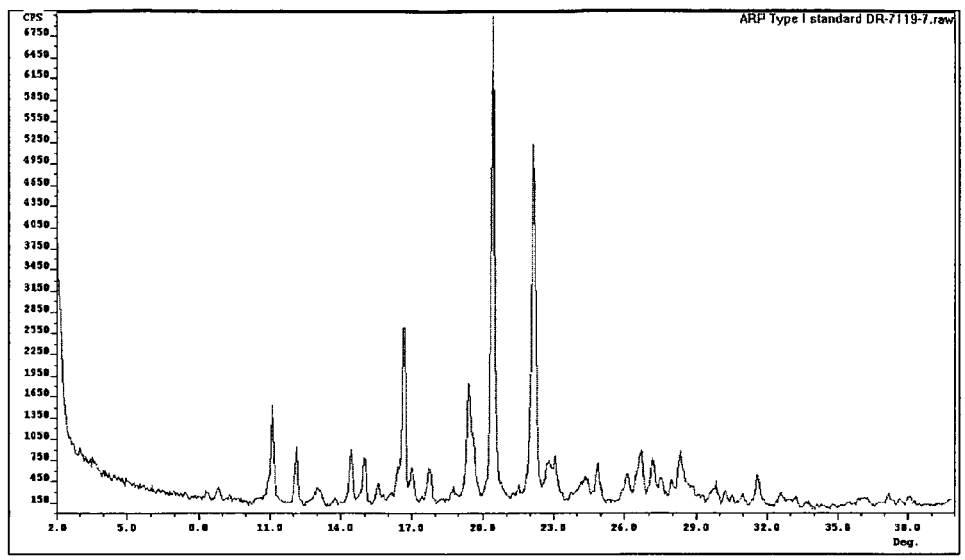
Figure 1. X-ray Diffractogram of Aripiprazole Type-I.
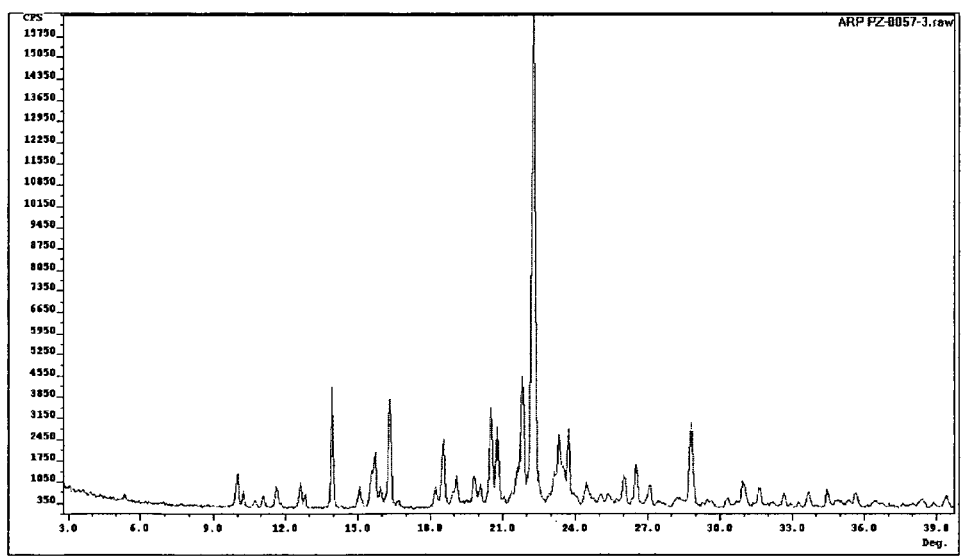
Figure 2. X-ray Diffractogram of Aripiprazole Type-II.

WET FORMULATIONS OF ARIPIPRAZOLE

RELATED APPLICATIONS

This application claims the benefit of U.S. provisional application Ser. No. 60/756,708, filed on Jan. 5, 2006.

FIELD OF THE INVENTION

The invention encompasses wet granulation pharmaceutical compositions of aripiprazole, methods of making tablets from the compositions, and tablets of the wet granulation pharmaceutical composition.

BACKGROUND OF THE INVENTION

Aripiprazole, as reported in the literature, can exist in multiple crystal forms. For example, PCT publication WO 03/026659 describes at least nine crystal forms, including an hydrate and anhydrous forms, such as Type-I and Type-II. According to WO 03/026659, the procedures disclosed in Proceedings of the 4th Japanese-Korean Symposium on Separation Technology (Oct. 6-8, 1996) yield significantly hydroscopic crystalline forms. The procedures disclosed in the Proceedings yield Type-I crystals of aripiprazole anhydride, prepared by recrystallizing from an ethanol solution of aripiprazole, or by heating aripiprazole hydrate at 80° C. The same Proceedings disclose that Type-II crystals of aripiprazole anhydride can be prepared by heating Type-I crystals of aripiprazole anhydride at 130° C. to 140° C. for 15 hours. In addition to Type-I and Type-II crystals, several additional anhydrous crystal forms are known. PCT publication WO 03/026659 discloses anhydride crystals Form B, C, D, E, F, or G and a hydrate form denominated Form A.

As reported in WO 03/026659, the multiple polymorphs may interconvert from one to the other. For instance, WO 03/026659 discloses that if the anhydrous form is exposed to moisture, then it may take on water and convert into a hydrous form. As stated in WO 03/026659, this presents several disadvantages, for instance the compound may be less bioavailable and less soluble. The hygroscopicity of aripiprazole crystals makes them difficult to handle since costly and burdensome measures must be taken to ensure that the crystals are not exposed to moisture during process and formulation. Despite these concerns, WO 03/026659 discloses a wet granulation process for preparing pharmaceutical compositions using aripiprazole anhydride and various carriers.

WO 03/026659 discloses the wet granulation of conventional aripiprazole anhydride crystals or anhydride Forms B, C, D, E, F, or G, drying the granules at 70° C. to 100° C. and sizing the granules, followed by drying the granules for a second time at a temperature of 70° C. to 100° C.

Other novel crystal aripiprazole forms are disclosed in PCT publication WO 05/058835. These other forms include Form I, II, VII, VIII, X, XI, XII, XIV, XIX, and XX.

Polymorphic transformations may be undesirable during pharmaceutical composition preparation or formulation. However, hydration or manipulation may induce unwanted polymorphic transformations. Also, the process during manufacture may introduce some aripiprazole polymorphs in pharmaceutical tablets other than the original starting material. The aripiprazole polymorphs may be unwanted polymorphs, which may reduce the bioavailability of the drug. Therefore, it would be desirable to develop methods for preparing aripiprazole formulations in which there is no potential of hydration and/or possible polymorphic interconversions.

SUMMARY OF THE INVENTION

In one embodiment, the invention encompasses a method of making tablets by wet granulation comprising: providing a mixture of aripiprazole, at least one diluent, at least one tablet binder, and water; blending the mixture to obtain a wet granulate; drying the wet granulate at a temperature less than 70° C. to obtain a dried granulate; and milling the dried granulate, with the proviso that the wet granulate is not milled prior to drying. Preferably, the wet granulate is dried at a temperature of about 60° C. or less. The method may further comprise adding at least one tablet lubricant to the dried milled granulate; and compressing the dried milled granulate to form tablets. The mixture may further comprise at least one colorant. In a preferred embodiment, the aripiprazole is at least one of anhydrous aripiprazole Type-I, Type-II, or Form II. The aripiprazole may have a particle size distribution where d(0.9) is about 300 μm or less.

Tablets made using the wet granulation formulation have a dissolution rate where not less than about 85% by weight of the initial aripiprazole is dissolved after about 30 minutes. Preferably, tablets made using the wet granulation formulation have a dissolution rate where not less than about 90% by weight of the initial aripiprazole is dissolved after about 30 minutes, and more preferably not less than about 95%.

In another embodiment, the diluent is calcium carbonate, calcium phosphate (dibasic and/or tribasic), calcium sulfate, powdered cellulose, dextrates, dextrin, fructose, kaolin, lactitol, anhydrous lactose, lactose monohydrate, maltose, mannitol, microcrystalline cellulose, sorbitol, sucrose, or starch. Preferably, the diluent is lactose monohydrate, microcrystalline cellulose, or starch. In one particular embodiment, the diluent is present in an amount of about 35% to about 90% by weight of the tablet.

In yet another embodiment, binder is acacia, alginic acid, carbomer, sodium carboxymethylcellulose, dextrin, ethylcellulose, gelatin, glucose, guar gum, hydroxypropyl cellulose, maltose, methylcellulose, polyethylene oxide, or povidone. Preferably, the binder is hydroxypropyl cellulose. In one particular embodiment, the binder is present in an amount of about 0.5% to about 5% by weight of the tablet.

In another embodiment, the lubricant is calcium stearate, glyceryl behenate, magnesium stearate, mineral oil, polyethylene glycol, sodium stearyl fumarate, stearic acid, talc, or zinc stearate. Preferably, the lubricant is magnesium stearate. In one particular embodiment, the lubricant is present in an amount of about 0.5% to about 2% by weight of the tablet.

In one embodiment, the invention encompasses a tablet comprising: aripiprazole Form II, lactose monohydrate, starch, microcrystalline cellulose, hydroxypropyl cellulose, color red, and magnesium stearate. In yet another embodiment, the invention encompasses a tablet comprising aripiprazole Type-I, lactose monohydrate, starch, microcrystalline cellulose, hydroxypropyl cellulose, and magnesium stearate.

BRIEF DESCRIPTION OF THE FIGURES

FIG. 1 illustrates the x-ray diffraction pattern of aripiprazole Type-I.

FIG. 2 illustrates the x-ray diffraction pattern of aripiprazole Type-II.

DETAILED DESCRIPTION OF THE INVENTION

The problems associated the hydration of aripiprazole during formulation or storage have focused research into developing stable anhydrous forms of aripiprazole. These forms would be less or non-hygroscopic, and thus resistant to hydration and the accompanying possible polymorphic transformation. The present invention provides an alternative solution to the development of stable anhydrous forms of aripiprazole. The present invention encompasses methods of wet granulating aripiprazole and methods of making tablets using the wet granulation methodology. The wet granulation methodology prevents or reduces hydration and, thus, the associated subsequent polymorphic transformations. Furthermore, unlike the prior art methods, the present method uses a temperature that allows for energy savings during the drying step.

The present invention encompasses methods of making tablets by wet granulation and tablets made using wet granulation methodology. Poorly compressible active ingredients may be formulated using wet granulation. Poorly compressible drugs include those with high molecular weights and relatively low glass transition temperatures (Tg), which will tend to stick to presses and/or have low cohesiveness. The advantages in wet granulating these active ingredients include improved free-flowing properties, homogeneity of the powder, better compressibility, and reduced dust during the processing.

Methods of wet granulating aripiprazole were developed, because it was found that anhydrous aripiprazole crystals were suitable for wet granulation. As used herein with the term "aripiprazole," the term "anhydrous" means aripiprazole is crystallized in a form, which does not contain solvent of crystallization or water incorporated within the crystal lattice, but may include water outside the crystal lattice.

The method for making tablets by wet granulation comprises providing a mixture of aripiprazole, at least one diluent, at least one tablet binder, and water; blending the mixture to obtain a homogeneous wet granulate; drying the wet granulate at a temperature less than 70° C. to obtain a dried granulate; milling the dried granulate; adding at least one tablet lubricant to the milled dried granulate; and compressing the dried granulate in a tablet press to obtain tablets, with the proviso that the wet granulate is not milled prior to drying. Optionally, at least one colorant may be added to the mixture to provide any desired colored tablet.

The method of mixing or blending the ingredients in the wet granulation can be carried out using methods known to the skilled artisan. With little or no experimentation, the skilled artisan can determine the conditions necessary to obtain the wet granulate. The skilled artisan will adjust the amount of water and time of granulation so that the granulate is of a size that does not require wet milling prior to drying as exemplified below.

The wet granulate is not milled prior to drying. In the process of the invention, the wet granulate is granulated as to reduce or remove lumps in the granulate. Therefore, the wet granulate can be dried as described below. Preferably, the drying is continued to obtain a loss on drying of about 1-2% without any additional sizing of the granules. The milled dried granulate has excellent flowability and can be easily compressed into tablets with hardness range of about 10 to 15 Strong-Cobb Units (SCU) and friability of less than 1.0%.

The drying step is carried out at temperature of about less than 70° C. Preferably, the drying step is carried out at an inlet temperature of about 60° C. or less.

The compressing step may be carried out using a tablet compression apparatus commonly used in tableting. For example, a Kilian tableting press may be used to form the tablets.

In a preferred embodiment, the method comprises blending aripiprazole Form II, lactose monohydrate, starch, microcrystalline cellulose, hydroxypropyl cellulose, and color red in a mixture, wet granulating the mixture using purified water as the granulation liquid; drying the wet granulate in a fluid bed dryer with an inlet temperature of about 65° C., milling the dried granulate using an oscillating granulator; blending magnesium stearate to the dried granulate; and compressing the second mixture into tablets. Preferably, the aripiprazole Form II had a d(0.9) value of about 25 μm.

Any aripiprazole may be used in the method of the invention. Typically, anhydrous aripiprazole may be used in the wet granulation method. Preferably, the anhydrous aripiprazole is at least one of Type-I, Type-II, or Form II. Type-I aripiprazole may be prepared by crystallization in ethanol and drying according to method described in WO 2005/058835. Alternatively, Type-I aripiprazole may be made according to the Reference Examples of WO 03/026659 and as described in the Proceedings of the 4$^{th}$ Japanese-Korean Symposium on Separation Technology (Oct. 6-8, 1996), both references hereby incorporated by reference. Type-II may be obtained by heating Type-I crystals of aripiprazole anhydride at 140° C. for 15 hours, according to the Reference Examples disclosed WO 03/026659. Form II aripiprazole may be prepared as disclosed in WO 05/058835.

Type-I aripiprazole is characterized by x-ray diffraction peaks at 8.8, 10.6, 11.1, 12.1, 15.0, 15.8, 17.7, 20.4, 22.1, and 29.8±0.2 degrees 2-theta. Type-II aripiprazole is characterized by x-ray diffraction peaks at 10.1, 11.7, 13.9, 15.1, 18.2, 20.8, 21.8, 23.5, 23.8, and 28.9±0.2 degrees 2-theta. The XRD diffractograms of aripiprazole Type-I and Type-II are shown in FIGS. 1 and 2, respectively. Form II aripiprazole is characterized by x-ray diffraction peaks at 16.5, 18.7, 21.9, 22.4, and 23.5±0.2 degrees 2-theta.

The crystal form of aripiprazole within the pharmaceutical compositions may be monitored using known state of the art techniques. For example, techniques such as X-ray powder diffraction (XRD) or solid-state NMR of carbon-13, nitrogen-14, or chlorine, among others, may be used. Generally, any instrumentation of X-ray powder diffraction or solid-state NMR normally available in laboratories is suitable for monitoring the crystal forms of aripiprazole in pharmaceutical compositions. Typical methods for obtaining X-ray diffractions of aripiprazole may be found in WO 03/026659 or WO 05/058835.

Optionally, the aripiprazole may have a particle shape. Typically, the particle size distribution d(0.9) is about 300 μm or less. If aripiprazole Type-I or Type-II is used, the particle size distribution d(0.9) is about 180 μm to about 270 μm. If aripiprazole Form II is used, the particle size distribution d(0.9) is about 25 μm.

The single dose of the active ingredient is small, and an inert substance may be added to increase the bulk and make the tablet a practical size for compression. Diluents are used for this purpose. Diluents used in the mixture include diluents commonly used for tablet preparation. For example, diluents include, but are not limited to, calcium carbonate, calcium phosphate (dibasic and/or tribasic), calcium sulfate, powdered cellulose, dextrates, dextrin, fructose, kaolin, lactitol, anhydrous lactose, lactose monohydrate, maltose, mannitol, microcrystalline cellulose, sorbitol, sucrose, or starch. Preferably, the diluent is lactose monohydrate, microcrystalline cellulose, or starch. Typically, the diluent is present in an amount of about 35% to about 90% by weight of the tablet. Preferably, the diluent is present in an amount of about 40% to about 85% by weight of the tablet.

Binders are agents used to impart cohesive qualities to the powdered material. Binders impart a cohesiveness to the tablet formulation that ensures that the tablet remain intact after compression. Tablet binders used in the mixture include tablet binders commonly used for tablet preparation. Tablet binders include, but are not limited to, acacia, alginic acid, carbomer, sodium carboxymethylcellulose, dextrin, ethylcellulose, gelatin, glucose, guar gum, hydroxypropyl cellulose, maltose, methylcellulose, polyethylene oxide, or povidone. Preferably, the tablet binder is hydroxypropyl cellulose. Typically, the tablet binder is present in an amount of about 0.5% to about 5% by weight of the tablet. Preferably, the tablet binder is present in an amount of about 0.7% to about 2% by weight of the tablet.

Lubricants have a number of functions in tablet manufacturing. For example, lubricants prevent adhesion of the tablet material to equipment, reduce interparticle friction, and facilitate the ejection of the tablet from the die cavity, among others. Tablet lubricants added to the milled dried granulate include those typically used in tablet formulations. Tablet lubricants include, but are not limited to, calcium stearate, glyceryl behenate, magnesium stearate, mineral oil, polyethylene glycol, sodium stearyl fumarate, stearic acid, talc, or zinc stearate. Preferably, the tablet lubricant is magnesium stearate. Typically, the tablet lubricant is present in an amount of about 0.5% to about 2% by weight of the tablet. Preferably, the tablet lubricant is present in an amount of about 0.7% to about 1% by weight of the tablet.

In one embodiment, the tablet made by the wet granulation method of the invention has a dissolution rate where not less than 85% by weight of the initial aripiprazole is dissolved after about 30 minutes. Preferably, the tablet made by the wet granulation method of the invention has a dissolution rate where not less than 90% by weight of the initial aripiprazole is dissolved after about 30 minutes, and more preferably, not less than 95% by weight. The test for dissolution is described below.

The invention also encompasses tablets made using the methodology described above. In one embodiment the tablet comprises aripiprazole, lactose monohydrate, starch, microcrystalline cellulose, hydroxypropyl cellulose, and magnesium stearate. Optionally, the tablet may further comprise a colorant. In another embodiment the tablet comprises aripiprazole Form II, lactose monohydrate, starch, microcrystalline cellulose, hydroxypropyl cellulose, and magnesium stearate. In a preferred embodiment the tablet comprises aripiprazole Form II (30 mg/tablet), lactose monohydrate (119 mg/tablet), starch (30 mg/tablet), microcrystalline cellulose (94 mg/tablet), hydroxypropyl cellulose (4 mg/tablet), magnesium stearate (2 mg/tablet), and color red (0.06 mg/tablet).

In yet another embodiment the invention encompasses a tablet comprising aripiprazole Type-I, lactose monohydrate, starch, microcrystalline cellulose, hydroxypropyl cellulose, and magnesium stearate. In a preferred embodiment, the invention encompasses a tablet comprising aripiprazole Type-I (30 mg/tablet), lactose monohydrate (120 mg/tablet), starch (60 mg/tablet), microcrystalline cellulose (60 mg/tablet), hydroxypropyl cellulose (8 mg/tablet), and magnesium stearate (2 mg/tablet).

Having described the invention with reference to certain preferred embodiments, other embodiments will become apparent to one skilled in the art from consideration of the specification. The invention is further defined by reference to the following examples describing in detail the wet granulation of aripiprazole and the dissolution of the tablets made using the wet granulate. It will be apparent to those skilled in the art that many modifications, both to materials and methods, may be practiced without departing from the scope of the invention.

EXAMPLES

Example 1

Preparation of 30 mg Tablets Containing Aripiprazole Form II Using Wet Granulation A mixture was made of aripiprazole Form II (210 g), lactose monohydrate NF (839.58 g), starch NF (210 g), microcrystalline cellulose NF (658 g), hydroxypropyl cellulose NF (28 g), and color red (0.42 g). The aripiprazole Form II had a D(0.9) value of about 25 μm. The mixture of materials was wet granulated using purified water as the granulation liquid. The wet granulate was dried in a fluid bed dryer with an inlet temperature of 65° C. Thereafter, the dried granulate was milled or "sized" using an oscillating granulator and blended for 10 minutes. Magnesium stearate NF (14 g) was sieved and added to the dried granulate and blended for an additional 5 minutes. Thereafter, the mixture was compressed into tablets using a Kilian tableting press.

Example 2

Preparation of 30 mg Tablets Containing Aripiprazole Type-I Using Wet Granulation A mixture was made of aripiprazole Type-I (105 g), lactose monohydrate NF (420 g), starch NF (210 g), microcrystalline cellulose NF (210 g), and hydroxypropyl cellulose NF (28 g). The mixture of materials was wet granulated using purified water as the granulation liquid. The wet granulate was dried in a fluid bed dryer with an inlet temperature of about 60° C. Thereafter, the dried granulate was milled or "sized" using an oscillating granulator and blended for 10 minutes. Magnesium stearate NF (7 g) was sieved and added to the blended mixture and blended for an additional 5 minutes. Thereafter, the mixture was compressed into tablets using a Kilian tableting press.

Example 3

Dissolution Measurements of Tablets Made in Examples 1 and 2

The dissolution for tablets from each of the above-described examples was studied. Typically, a the dissolution rate was measured for each batch after 30 minutes. The dissolution was carried out using an USP apparatus II (paddle) at 60 rpm with 900 ml of 0.1 N HCl at a temperature of 37° C. The results are summarized in Table 1.

TABLE 1

| Measurement of Aripiprazole Dissolved from Examples 1-2 | | | |
| --- | --- | --- | --- |
| Example No. | Time (minutes) | Average Dissolution* | Minimum Dissolution* |
| 1 | 30 | 99 | 99 |
| 2 | 30 | 98 | 95 |

*Average dissolution and minimum dissolution are reported as a percent by weight of the labeled amount.

What is claimed is:

1. A method of making an aripiprazole pharmaceutical composition by wet granulation comprising:
   providing a mixture of aripiprazole, at least one diluent, at least one tablet binder, and water;
   blending the mixture to obtain a wet granulate;

drying the wet granulate at a temperature of less than 70° C. to obtain a dried granulate; and milling the dried granulate to obtain the pharmaceutical composition comprising a milled dried granulate, with the proviso that the wet granulate is not milled prior to drying, wherein the aripiprazole is anhydrous aripiprazole.

2. The method according to claim 1, wherein the drying step temperature is 60° C. or less.

3. The method according to claim 1, further comprising the steps of:

adding at least one tablet lubricant to the milled dried granulate; and compressing the milled dried granulate in a tablet press to obtain a tablet.

4. The method according to claim 1, wherein the mixture further comprises at least one colorant.

5. The method according to claim 1, wherein the aripiprazole is at least one of anhydrous aripiprazole Type-I, Type-II, or Form II.

6. The method according to claim 1, wherein the aripiprazole has a particle size distribution where d(0.9) is about 300 μm or less.

7. The method according to claim 1, wherein the diluent is calcium carbonate, calcium phosphate (dibasic and/or tribasic), calcium sulfate, powdered cellulose, dextrates, dextrin, fructose, kaolin, lactitol, anhydrous lactose, lactose monohydrate, maltose, mannitol, microcrystalline cellulose, sorbitol, sucrose, or starch.

8. The method according to claim 1, wherein the diluent is lactose monohydrate, microcrystalline cellulose, or starch.

9. The method according to claim 1, wherein the diluent is present in an amount of about 35% to about 90% by weight of the tablet.

10. The method according to claim 1, wherein the binders is acacia, alginic acid, carbomer, sodium carboxymethylcellulose, dextrin, ethylcellulose, gelatin, glucose, guar gum, hydroxypropyl cellulose, maltose, methylcellulose, polyethylene oxide, or povidone.

11. The method according to claim 1, wherein the binder is hydroxypropyl cellulose.

12. The method according to claim 1, wherein the binder is present in an amount of about 0.5% to about 5% by weight of the composition.

13. The method according to claim 3, wherein the lubricant is calcium stearate, glyceryl behenate, magnesium stearate, mineral oil, polyethylene glycol, sodium stearyl fumarate, stearic acid, talc, or zinc stearate.

14. The method according to claim 3, wherein the lubricant is magnesium stearate.

15. The method according to claim 3, wherein the lubricant is present in an amount of about 0.5% to about 2% by weight of the tablet.

16. The method according to claim 3, wherein the tablet has a dissolution rate where not less than 85% by weight of the initial aripiprazole is dissolved after about 30 minutes.

17. The method according to claim 3, wherein the tablet has a dissolution rate where not less than 90% by weight of the initial aripiprazole is dissolved after about 30 minutes.

18. The method according to claim 3, wherein the tablet has a dissolution rate where not less than 95% by weight of the initial aripiprazole is dissolved after about 30 minutes.

19. A method for making aripiprazole pharmaceutical compositions by wet granulation comprising:

blending aripiprazole Form II, lactose monohydrate, starch, microcrystalline cellulose, hydroxypropyl cellulose, and color red in a mixture;

wet granulating the mixture using water as the granulation liquid;

drying the wet granulate in a fluid bed dryer with an inlet temperature of 65° C. or less;

milling the dried granulate using an oscillating granulator;

blending magnesium stearate to the dried granulate to form a second mixture; and compressing the second mixture into tablets.

20. The method according to claim 19, wherein the aripiprazole Form II has a d(0.9) value of about 25 μm.

21. The method according to claim 1, wherein the drying step temperature is 65° C. or less.

22. The method according to claim 19, wherein the drying step temperature is 65° C.

\* \* \* \* \*